United States Patent [19]

Kalopissis et al.

[11] 4,031,160
[45] June 21, 1977

[54] 2-AMINO-4-HYDROXY-5-CHLORO TOLUENE AND THE HYDROCHLORIDE THEREOF

[75] Inventors: Gregoire Kalopissis, Paris; Andree Bugaut, Boulogne-sur-Seine, both of France

[73] Assignee: Societe Anonyme dite: L'Oreal, Paris, France

[22] Filed: June 30, 1975

[21] Appl. No.: 592,051

Related U.S. Application Data

[63] Continuation of Ser. No. 273,810, July 21, 1972, abandoned, which is a continuation of Ser. No. 841,569, July 14, 1969, abandoned, which is a continuation-in-part of Ser. No. 525,291, Feb. 7, 1966, Pat. No. 3,591,323.

[30] Foreign Application Priority Data

May 6, 1965 France ............................ 65.16140

[52] U.S. Cl. .................................. 260/575; 8/10.2; 8/11; 8/25; 8/26
[51] Int. Cl.$^2$ ................... C07C 91/42; A61K 7/12; D06P 1/32
[58] Field of Search ...................... 260/575; 8/10.2

[56] References Cited

UNITED STATES PATENTS 3,558,259  7/1963  Kalopissis et al. .................... 8/10.2

OTHER PUBLICATIONS

Beilstein, "Handbuch der Organischen Chemie," Band 4, vol. 13, 2nd supplement, pp. 338 and 340 (1950).
Wilson et al., "J. Electrochem. Soc.", vol. 99, pp. 289–294 (1952).
Hodgson et al., "J. Chem. Soc.", pp. 2036–2040 (1926).
Raiford et al., "J. Am. Chem. Soc.", vol. 55, pp. 2125–2131 (1933).
Guyader et al., "Compt. Rend.," vol. 25, t. 259, pp. 4719–4721 (1964).
Angeletti et al.(I), "Chem. Abstracts," vol. 35, p. 3249a (1941).
Auwers et al., "Chem. Abstracts," vol. 19, p. 2339$^8$ (1925).
Angeletti et al.(II), "Chem. Abstracts," vol. 35, p. 6248$^9$ (1941).

Primary Examiner—Daniel E. Wyman
Assistant Examiner—John J. Doll
Attorney, Agent, or Firm—Cushman, Darby & Cushman

[57] ABSTRACT

2-Amino-4-hydroxy-5-chloro toluene and the hydrochloride thereof are couplers usefully employed in the production of a hair dye by reaction with an aromatic paradiamine.

2 Claims, No Drawings

2-AMINO-4-HYDROXY-5-CHLORO TOLUENE AND THE HYDROCHLORIDE THEREOF

This is a continuation, of application Ser. No. 273,810 filed July 21, 1972 abandoned which is a continuation of Ser. No. 841,569 filed July 14, 1969 abandoned which is a continuation-in-part of Ser. No. 525,291, filed Feb. 7, 1966 now U.S. Pat. No. 3,591,323.

SUMMARY OF THE INVENTION

Hair dyes having a substituted or unsubstituted aromatic diamine base have been used for a long time. The substitutions are on the aromatic ring or the nitrogen atoms of the amino groups. Coupling substances are added to these diamine bases to vary the color obtained.

It is known that the addition of certain coupling substances to such aromatic paradiamines makes it possible to obtain particularly stable and long-lasting colorations, while the shades obtained with the bases alone change rapidly. Moreover, certain of these bases are not dyes in themselves, but are effective only when suitably coupled.

Among the known substances conventionally coupled with aromatic paradiamines is meta-aminophenol, which unfortunately frequently produces hair dyes which do not last very long. The present invention proposes a new class of meta-amino-phenols for use as coupling substances, which make it possible to obtain especially stable long-lasting colorations, which resist exposure to the light and to outside agents, and enlarge the range of shades in the blue section of the spectrum which may be obtained by associating an aromatic paradiamine and a meta-amino-phenol.

The object of the present invention is to provide coupling compounds which form new dyes for keratinic fibers, and particularly for hair, said new dyes are essentially characterized by the fact that they are the reaction product of at least one aromatic paradiamine having the formula:

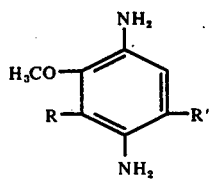
(I)

in which R and R' are hydrogen or methyl, but R' cannot be hydrogen when R is methyl, and
a meta-amino-phenol coupling substance having the formula:

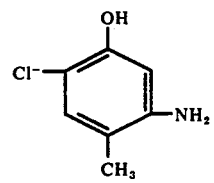
(II)

This invention is directed to the new coupling compound of formula II set forth above and the compounds it forms when it reacts with the compounds of formula I.

A characteristic feature of the invention resides in the fact that in the dyeing solution the ratio between the molecular concentration of the bases used and that of the coupling substances used is generally close to, but preferably less than 1.

If the coupling compound of formula II is not present in a molar excess with relation to the base compound of formula I the hair dye compositions tend to cause toxic or allergy reactions when they contact the skin. When these compositions contain a molar excess of the coupling compound the dye compositions do not cause toxic or allergy reactions.

The said dyeing solution is utilized in a conventional manner, by bringing it to an alkaline pH, with ammonia, for example, and applying it to the hair in the presence of an oxidizing solution which preferably is a hydrogen peroxide solution.

The dyeing solution may also contain other dyes which may be used under the same conditions as direct dyes for keratinic fibers, for example azo or anthraquinone dyes, or dyes obtained by associating bases and coupling substances other than those with which the present invention is concerned.

The dyeing solutions may also contain wetting, dispersing or penetrating agents, and other ingredients commonly included in hair dyes. The product may take the form of an aqueous solution, a cream or a gel.

A very broad range of colors within the blue portion of the spectrum may be obtained by associating a coupling substance of this invention with an aromatic paradiamine, and when an aromatic paradiamine is used with a combination of two coupling substances according to the invention all the shades between those which can be obtained by associating any of the single coupling substances with the base may be secured by varying the proportion between the two coupling substances.

Another object of the invention is the new method of dyeing the hair with these new hair dye compositions which comprises the steps of adding hydrogen peroxide, applying a dye of the above-defined type, and then rinsing, shampooing, washing and drying the hair.

A still further object of the invention is to provide new methods preparing the meta-amino-phenols responding to formula II.

The process of preparing 2-nitro-4-hydroxy-toluene is essentially characterized by the fact that paracresol is reacted with an agent capable of protecting the phenol function, preferably with methane sulfochloride. The benzene ring is nitrated in the meta position with respect to the phenol function, for example, with a sulfanitric mixture and the phenol function is then liberated with, for example, a sodium hydroxide solution.

The process of preparing 2-amino-4-hydroxy-5-chlorotoluene is essentially characterized by the fact that a reducing mixture formed from hydrochloric acid and tin is caused to set on the 2-nitro-4-hydroxy toluene. In this process the reducing mixture simultaneously reduces the nitro group of the starting preparation and causes chlorination in the para position with respect to the original nitro group.

In order that the invention may be clearly understood, several illustrative methods of carrying it out will now be described.

EXAMPLE 1

Preparation of 2-nitro-4-hydroxy toluene

This process embodies the reaction shown in the following diagram:

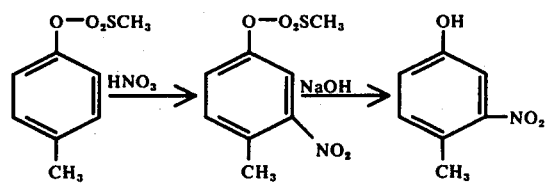

In a first step 4-hydroxy toluene is mesylated by reacting methane sulfochloride and paracresol.

In a second step 2-nitro-4-mesyloxy toluene is prepared by dissolving 0.1 mol (18.6 g) of mesylated 4-hydroxy toluene at a low temperature (0° to 5° C) in 80 cm³ of concentrated sulfuric acid. A sulfo-nitric mixture having the following composition is added at the same temperature:

| | |
|---|---|
| Nitric acid (density 1.49) | 4.7 cm³ |
| Sulfuric acid (density 1.83) | 3.8 cm³ |

The reaction mixture is then poured over ice and the crude product of the reaction dried. After recrystallization in ethanol, the product melts at 105°–106° C. The yield of the reaction is about 89%. Analysis shows the following results:

| Analysis | Calculated for $C_8H_9O_5NS$ | Found |
|---|---|---|
| C% | 41.6 | 41.40–41.57 |
| H% | 3.90 | 3.90–4.06 |
| N% | 6.06 | 6.13–6.10 |

In a third step, 2-nitro-4-hydroxy toluene is prepared by reacting 10 mol (23.1 g) of 2-nitro-4-mesyloxy toluene with 95 cm³ of sodium hydroxide at triple normal strength, under reflux for 2 hours in a nitrogen atmosphere. After cooling with 50 g of ice, the solution is neutralized with hydrochloric acid and 15.3 g of 2-nitro-4-hydroxy toluene are dried. The product, melts at 77° C.

EXAMPLE 2

Preparation of 2-amino-4-hydroxy-5-chloro toluene

The process embodies the reaction shown in the following diagram:

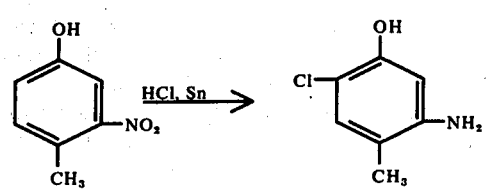

0.5 mol (76.5 g) of 2-nitro-4-hydroxy toluene is reduced with a mixture containing 600 cm³ of concentrated hydrochloric acid and 116 g of tin at 75°–80° C. This is filtered while hot, yielding 45 g of 2-amino-4-hydroxy-5 chloro toluene hydrochloride, which is insoluble in concentrated hot hydrochloric acid. The hydrochloric solution of the reduction contains 2-amino-4-hydroxy toluene as chlorostannate. 2-amino-4-hydroxy toluene, which melts at 159° C, may be isolated, if desired.

The 2-amino-4-hydroxy-5-chloro toluene hydrochloride thus obtained is dissolved in water. The solution is alkalized with ammonia and drying yields 33.8 g of 2-amino-4-hydroxy-5-chloro toluene, which after recrystallization in benzene, melts at 144.5° C.

| Analysis | Calculated for $C_7H_8ONCl$ | Found |
|---|---|---|
| C% | 53.33 | 53.33–53.60 |
| H% | 5.07 | 5.08–5.02 |
| N% | 8.88 | 9.07–9.03 |

EXAMPLE 3

The following solution is prepared:

| | |
|---|---|
| 2-amino-4-hydroxy-5-chloro toluene | 0.32 g |
| 2,5-diamino-4-methyl-1-methoxy benzene dihydrochloride | 0.45 g |
| Ammonium lauryl sulfate (having 20% fatty alcohol) | 10.00 g |
| Ammonia at 20% concentration in water | 7 cm³ |
| Water, q.s.p. | 100 g |

This solution is mixed with an equal volume of a 6% by weight hydrogen peroxide solution and applied to white hair. After 20 minutes, the hair is shampooed, rinsed and dried. An intense violet shade results.

EXAMPLE 4

The following solution was prepared:

| | |
|---|---|
| 2-amino-4-hydroxy-5-chloro toluene | 1.5 g |
| 3,6-diamino-2,4 dimethyl anisol dihydrochloride | 2.2 g |
| Ammonia at 20% concentration in water | 10 cm³ |
| Alcohol at 95° | 10 cm³ |
| Water, q.s.p. | 100 cm³ |

This solution is mixed with an equal volume of a 6% by weight hydrogen peroxide solution. The mixture is applied to 100% white hair. After 20 minutes the hair is shampooed, rinsed and dried. An intense bluish violet shade, which is stable when exposed to the light, results.

EXAMPLE 5

The following solution is prepared:

| | |
|---|---|
| 3,6-diamino-2,4-dimethyl anisol dihydrochloride | 16.6 g |
| 2-amino-4-hydroxy-5-chlorotoluene | 15.75 g |
| Ammonium lauryl sulfate at 20% concentration in water | 200 g |
| Carboxymethylcellulose | 20 g |
| Sodium bisulfite | 4 g |
| Ethylene diamino tetra-acetic acid | 3 g |
| Ammonia at 20% concentration in water | 100 cm³ |
| Water q.s.p. | 1000 g |

This mixture is a thick liquid. It is diluted, when used, with an equal volume of hydrogen peroxide and applied to 90% white hair. After 30 minutes the hair is rinsed, shampooed, and dried. An intense violine shade, which is stable when exposed to the light, results.

EXAMPLE 6

The following solution is prepared:

| | |
|---|---|
| 3,6-diamino-2,4-dimethyl anisol dihydrochloride | 8.3 g |
| 2-amino-4-hydroxy-5-chloro toluene | 7.8 g |
| Ammonium lauryl sulfate at 20% concentration in water | 200 g |
| Carboxymethylcellulose | 20 g |
| Disodium salt of ethylene diamino tetra-acetic acid (Trilon B) | 3 g |
| Sodium bisulfite | 4 g |
| Ammonium at 20% concentration in water | 100 cm$^3$ |
| Water, q.s.p. | 1000 g |

This solution is mixed with an equal volume of a 6% by weight hydrogen peroxide solution and applied to 90% white hair. After waiting 30 minutes the hair is rinsed, shampooed and dried. The result is a mahogany violine shade, which is stable when exposed to the light.

What is claimed is:

1. 2-amino-4-hydroxy-5-chloro toluene and its hydrochloride salt.

2. The compound of claim 1, which is 2-amino-4-hydroxy-5-chloro toluene.

* * * * *